United States Patent
Li (10) Patent No.: US 9,905,004 B2
(45) Date of Patent: Feb. 27, 2018

(54) IMAGE PROCESSING DEVICE, METHOD, AND RECORDING MEDIUM HAVING STORED THEREIN PROGRAM

(71) Applicant: FUJIFILM Corporation, Tokyo (JP)

(72) Inventor: Yuanzhong Li, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/277,082

(22) Filed: Sep. 27, 2016

(65) Prior Publication Data

US 2017/0018079 A1   Jan. 19, 2017

Related U.S. Application Data (63) Continuation of application No. PCT/JP2015/001460, filed on Mar. 17, 2015.

(30) Foreign Application Priority Data

Mar. 31, 2014   (JP) .................................. 2014-072141

(51) Int. Cl.
*G06T 7/00* (2017.01)
*A61B 5/00* (2006.01)
(Continued)

(52) U.S. Cl.
CPC ............ *G06T 7/0012* (2013.01); *A61B 5/004* (2013.01); *A61B 5/055* (2013.01); *A61B 5/08* (2013.01);
(Continued)

(58) Field of Classification Search
None
See application file for complete search history.

(56) References Cited

U.S. PATENT DOCUMENTS

| | | | |
|---|---|---|---|
| 2007/0025508 A1* | 2/2007 | Ohishi | A61B 6/4441 378/62 |
| 2008/0118135 A1 | 5/2008 | Averbuch et al. | |
| 2016/0328846 A1* | 11/2016 | Trousset | G06T 19/003 |

FOREIGN PATENT DOCUMENTS

| | | |
|---|---|---|
| JP | 2010-510815 A | 4/2010 |
| JP | 2013-192741 A | 9/2013 |
| WO | WO 2013/118047 A1 | 8/2013 |

OTHER PUBLICATIONS

Criminisi et al., "Regression Forests for Efficient Anatomy Detection and Localization in CT Studies", Medical Computer Vision. Recognition Techniques and Applications in Medical Imaging, Lecture Notes in Computer Science, vol. 6533, 2011, pp. 106-117.
(Continued)

*Primary Examiner* — Chan Park
*Assistant Examiner* — Geoffrey E Summers
(74) *Attorney, Agent, or Firm* — Birch, Stewart, Kolasch & Birch, LLP (57) ABSTRACT

A target place is set in an area of a human body structure having a tree structure in a three-dimensional image. The tree structure of the human body structure is extracted. A path from a reference point set on a branch upstream side of the target place on the tree structure to the target place is determined. Priority is set for respective portions of the tree structure of the human body structure outside the path based on a positional relationship between the portions and the target place. An initial image representing only a portion of the path and images for confirmation of each step sequentially representing the respective portions of the human body structure outside the path according to the priority are generated from the three-dimensional image. The initial image is displayed, and then, the generated images for confirmation of each step are displayed.

11 Claims, 9 Drawing Sheets

(51) Int. Cl.
  *A61B 5/055*  (2006.01)
  *A61B 5/08*  (2006.01)
  *G06T 19/00*  (2011.01)
  *A61B 6/00*  (2006.01)
  *A61B 6/03*  (2006.01)

(52) U.S. Cl.
  CPC .............. *A61B 5/489* (2013.01); *A61B 5/742* (2013.01); *A61B 6/504* (2013.01); *A61B 6/5217* (2013.01); *G06T 19/00* (2013.01); *A61B 6/032* (2013.01); *A61B 6/465* (2013.01); *A61B 6/466* (2013.01); *A61B 6/469* (2013.01); *A61B 6/503* (2013.01); *A61B 6/505* (2013.01); *A61B 2576/02* (2013.01); *G06T 2207/10072* (2013.01); *G06T 2207/10081* (2013.01); *G06T 2207/30061* (2013.01); *G06T 2210/41* (2013.01)

(56) References Cited

OTHER PUBLICATIONS

International Search Report (PCT/ISA/210) issued in PCT/JP2015/001460, dated Jul. 14, 2015.

Kitamura et al., "Automatic Coronary Extraction by Supervised Detection and Shape Matching", Proc. IEEE ISBI, 2012, pp. 234-237.

Written Opinion (PCT/ISA/237) issued in PCT/JP2015/001460, dated Jul. 14, 2015.

\* cited by examiner

IMAGE PROCESSING DEVICE, METHOD, AND RECORDING MEDIUM HAVING STORED THEREIN PROGRAM

CROSS-REFERENCE TO RELATED APPLICATIONS

This application is a Continuation of PCT International Application No. PCT/JP2015/001460 filed on Mar. 17, 2015, which claims priority under 35 U.S.C. § 119(a) to Japanese Patent Application No. 2014-072141 filed on Mar. 31, 2014. Each of the above applications is hereby expressly incorporated by reference, in its entirety, into the present application.

BACKGROUND OF THE INVENTION

1. Field of the Invention

The present invention relates to an image processing device and method, and a recording medium having stored therein a program which provide an image for observing a place of interest in a human body structure having a tree structure.

2. Description of the Related Art

Hitherto, in the medical field, in order to facilitate observation of a three-dimensional structure of a human body structure having a tree structure, for example, a blood vessel, a bronchus, or the like, processing for generating and displaying a pseudo three-dimensional image, such as a surface-rendering image (SR image) or a volume-rendering image (VR image), in which a target human body structure is stereoscopically drawn, from a three-dimensional image of a subject obtained by a modality, such as a computed tomography (CT) apparatus, a magnetic resonance imaging (MRI) apparatus, or an ultrasound diagnostic apparatus, has been performed.

JP2013-192741A and JP2010-510815A describe that an image in which a path from the root of a bronchus to a lesion is displayed on an SR image or a VR image, in which a bronchus is drawn, in a superimposed manner is provided.

SUMMARY OF THE INVENTION

However, in the technique of the related art, since the entire target human body structure in the SR image or the VR image is a target to be drawn, there is a problem in that a place of interest is obstructed by a surrounding structure and is difficult to observe when the three-dimensional running or distribution of the target human body structure is complicated.

The invention has been accomplished in consideration of the above-described situation, and an object of the invention is to provide an image processing device, method, and program for, in a three-dimensional image obtained by imaging a human body structure having a tree structure, allowing easy understanding of what anatomical region a place of interest on a human body structure is or what kind of anatomical structure there is around the place.

An image processing device of the invention comprises a target place setting unit which sets a target place in an area of a human body structure having a tree structure in a three-dimensional image obtained by imaging the human body structure, a tree structure acquisition unit which acquires the tree structure of the human body structure in the three-dimensional image, a path determination unit which determines a path from a reference point set on a branch upstream side of the target place on the acquired tree structure to the target place, an image generation unit which generates, from the three-dimensional image, an initial image representing only a portion of the determined path in the entire human body structure and images for confirmation of each step sequentially representing the respective portions of the human body structure outside the determined path according to the priority determined based on the positional relationship with the target place, a display unit which displays an image, and a display control unit which displays the generated initial image on the display unit and then displays the generated images for confirmation on the display unit such that the respective portions of the human body structure outside the path are sequentially displayed according to the priority determined based on the positional relationship with the target place.

The branch upstream side of the target place on the tree structure means a side toward the root of the tree structure from the target place through the branch of the branch source.

The image processing device of the invention may further comprise a priority setting unit which sets the priority such that, the closer the position of the branch to the target place, the higher the priority of each branch of the tree structure branching from the determined path, the image generation unit may generate, from the three-dimensional image, the images for confirmation of each step in which the portions of the respective branches of the human body structure branching from the path are displayed in an order of priority determined by the priority setting unit, and the display control unit may display the images for confirmation on the display unit such that the portions of the respective branches of the human body structure branching from the path are displayed in the order of priority determined by the priority setting unit.

In the image processing device of the invention, in a case where there are a plurality of branches at the same branch position branching from the determined path, the priority setting unit may set the priority such that, the shorter the distance between a middle point of the branch and a middle point of a branch including the target place, the higher the priority. The middle point of the branch means a point which is on a line segment with a start point and an end point of the branch as both ends, and is at the same distance from both ends.

The priority setting unit may have a table in which the priority of each branch is determined in advance for each group of branches branching at the same position on the tree structure, and in a case where there are a plurality of branches at the same branch position branching from the determined path, may set the priority determined in the table.

In the image processing device of the invention, the display control unit may display the images for confirmation in a display order according to an input from an operator instructing to display the images for confirmation in the display order such that the portions of the respective branches of the human body structure branching from the path are displayed in a descending order of priority and may display the images for confirmation in a reverse display order to the display order according to an input from the operator instructing to display the images for confirmation in the reverse display order to the display order.

In the image processing device of the invention, in a case where an aorta is included in the human body structure and the target place is an artery, the path determination unit may determine the path by setting the reference point at a position corresponding to the aorta on the tree structure. In a case where a vena cava is included in the human body structure and the target place is a vein, the path determination unit may determine the path by determining the reference point at a position corresponding to the vena cava on the tree structure. In a case where the region of origin of a portal vein is included in the human body structure and the target place is the portal vein, the path determination unit may determine the path by setting the reference point at a position corresponding to the region of origin of the portal vein on the tree structure. The path determination unit may determine the path by setting the reference point at a position of a starting point of the acquired tree structure.

The image processing device of the invention may further comprise a region specification unit which specifies a region of a human body, to which the target place belongs, and a storage unit which stores a table, in which each region of the human body and a display range are made to correspond to each other, and the image generation unit may generate the initial image and the images for confirmation of each step representing the display range corresponding to the specified region of the human body from the three-dimensional image based on the table.

In this case, the path determination unit may determine the path by setting the reference point at an uppermost position in the tree structure within the display range corresponding to the specified region of the human body.

An image processing method of the invention comprises a step of setting a target place in an area of a human body structure having a tree structure in a three-dimensional image obtained by imaging the human body structure, a step of acquiring the tree structure of the human body structure in the three-dimensional image, a step of determining a path from a reference point set on a branch upstream side of the target place on the acquired tree structure to the target place, a step of generating, from the three-dimensional image, an initial image representing only a portion of the determined path in the entire human body structure and images for confirmation of each step sequentially representing the respective portions of the human body structure outside the determined path according to the priority determined based on the positional relationship with the target place, and a step of displaying the generated initial image on a display unit and then displaying the generated images for confirmation on the display unit such that the respective portions of the human body structure outside the path are sequentially displayed according to the priority determined based on the positional relationship with the target place.

An image processing program of the invention causes a computer to function as a target place setting unit which sets a target place in an area of a human body structure having a tree structure in a three-dimensional image obtained by imaging the human body structure, a tree structure acquisition unit which acquires the tree structure of the human body structure in the three-dimensional image, a path determination unit which determines a path from a reference point set on a branch upstream side of the target place on the acquired tree structure to the target place, an image generation unit which generates, from the three-dimensional image, an initial image representing only a portion of the determined path in the entire human body structure and images for confirmation of each step sequentially representing the respective portions of the human body structure outside the determined path according to the priority determined based on the positional relationship with the target place, and a display control unit which displays the generated initial image on the display unit and then displays the generated images for confirmation on the display unit such that the respective portions of the human body structure outside the path are sequentially displayed according to the priority determined based on the positional relationship with the target place.

The image processing program typically has a plurality of program modules, and the functions of the respective units described above are realized by one or a plurality of program modules. The program module group is recorded on a recording medium, such as a CD-ROM or a DVD, or is recorded in a state of being downloadable to a storage or a network storage attached to a server computer and is provided to the user.

According to the image processing device, method, and program of the invention, the target place is set in the area of the human body structure in the three-dimensional image obtained by imaging the human body structure having the tree structure, the tree structure of the human body structure in the three-dimensional image is acquired, the path from the reference point set on the branch upstream side of the target place on the acquired tree structure to the target place is determined, the initial image representing only the portion of the determined path in the entire human body structure and the images for confirmation of each step sequentially representing the respective portions of the human body structure outside the determined path according to the priority determined based on the positional relationship with the target place are generated from the three-dimensional image, and the generated initial image is displayed on the display unit and then the generated images for confirmation are displayed on the display unit such that the respective portions of the human body structure outside the path are sequentially displayed according to the priority determined based on the positional relationship with the target place. With this display, it is possible to allow the user to easily understand what anatomical region a place of interest on a human body structure is or what kind of anatomical structure there is around the place.

DESCRIPTION OF THE PREFERRED EMBODIMENTS

Figure 1:
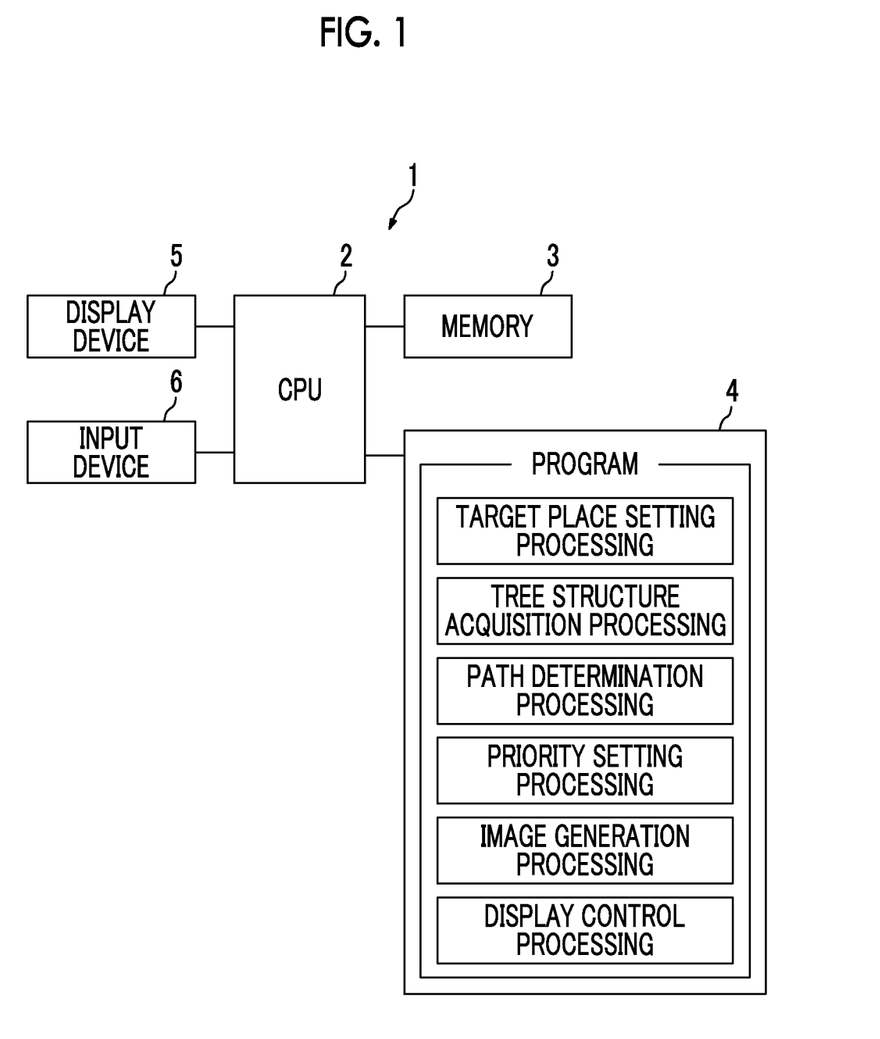
FIG. 1 is a diagram showing the schematic configuration of an image processing device according to a first embodiment.

Hereinafter, an embodiment of the invention will be described referring to the drawings. An image processing device 1 according to a first embodiment of the invention is realized by an image processing program which is loaded and executed on a computer. As shown in FIG. 1, the image processing device 1 comprises a central processing unit (CPU) 2 and a memory 3, and further comprises a storage 4, such as a hard disk drive (HDD). A display device 5 (display unit), such as a display, and an input device 6, such as a mouse and a keyboard, are connected to the image processing device 1.

Figure 2:
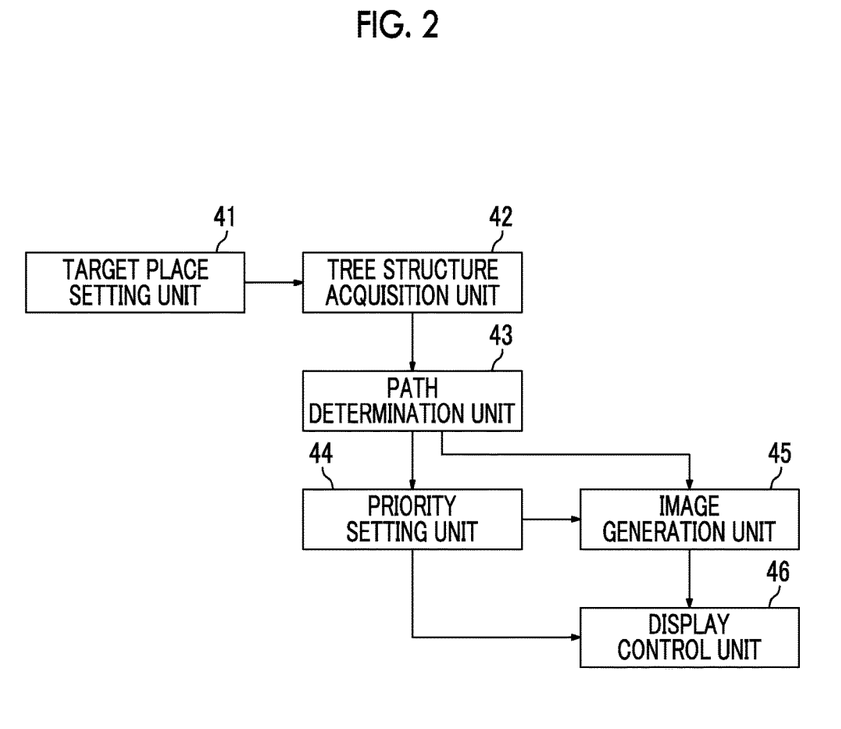
FIG. 2 is a block diagram showing functions mounted in the image processing device of FIG. 1.

The image processing program and data referred to by the image processing program are stored in the storage 4 and are loaded in the memory during start. The image processing program defines, as processing to be executed on the CPU, target place setting processing, tree structure acquisition processing, path determination processing, priority setting processing, image generation processing, and display control processing. According to the definition of the program, the CPU executes the respective kinds of processing, whereby the computer functions as a target place setting unit 41, a tree structure acquisition unit 42, a path determination unit 43, a priority setting unit 44, an image generation unit 45, and a display control unit 46 as shown in FIG. 2. FIG. 2 schematically shows the functions mounted in the image processing device 1 into blocks.

The target place setting unit 41 sets a target place in an area of a human body structure in a three-dimensional image of a patient obtained by imaging a human body structure having a tree structure, such as a bronchus, a blood vessel, or a bone. At this time, it is assumed that the three-dimensional image is captured in CT inspection or MRI inspection and is stored in the storage 4. The target place setting unit 41 can set the target place automatically or manually. In a case of automatic setting, the computer can execute processing for automatically detecting a part, which is suspected to be a lesion part on the human body structure, from the three-dimensional image by image analysis, and can set the detected part or one section of the human body structure including this part as the target place. For example, in a case where a narrow part in a blood vessel is automatically detected, it is possible to set, as the target place, the detected narrow part or a blood vessel branch where the narrow part is positioned.

In a case of manual setting, sliced tomographic images constituting the three-dimensional image can be sequentially displayed on the display device 5, an input from the user to designate a part to be observed on the human body structure in any displayed tomographic image can be received, and the designated part or one section of the human body structure including this part can be set as the target place. For example, an input from the user to designate a part to be observed in a blood vessel can be received, and the designated part or a blood vessel branch including this part can be set as the target place.

The tree structure acquisition unit 42 acquires the tree structure of the human body structure including the set target place from the three-dimensional image of the patient. The tree structure acquisition unit 42 can extract the tree structure of the target human body structure from the three-dimensional image of the patient, for example, using an automatic extraction method of a tree structure described in Y. Kitamura et al., "Automatic coronary extraction by supervised detection and shape matching", Proc. IEEE ISBI, pp. 234-237, 2012. Specifically, a plurality of candidate points belonging to the target human body structure are extracted from image data, a graph is created by connecting the extracted candidate points, and a shape model of the tree structure representing a general shape of the target human body structure is fitted to the created graph, thereby extracting the tree structure of the human body structure. In a case where the tree structure of the target human body structure is extracted from the three-dimensional image of the patient in advance and stored in the storage 4 or the like, the tree structure of the human body structure can be acquired from the storage 4 or the like by reading information of the tree structure of the human body structure.

Figure 3:
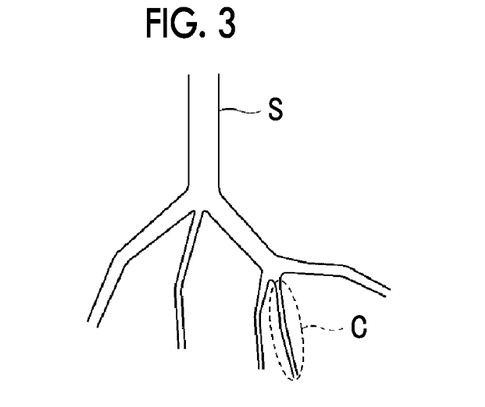
FIG. 3 is a diagram showing an example of a human body structure in which a target place is set.
Figure 4:
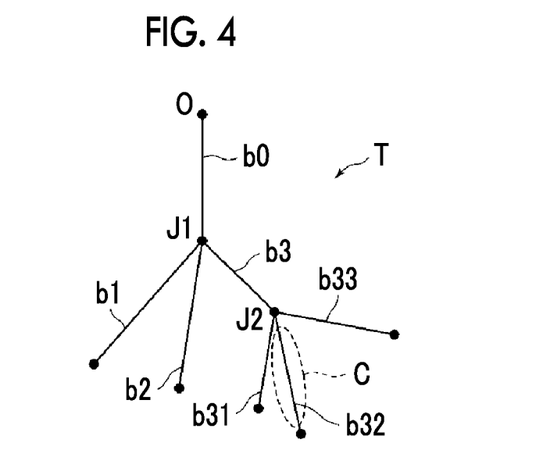
FIG. 4 is a diagram showing a tree structure of the human body structure of FIG. 3.

For example, as shown in FIG. 3, in a case where a target place C is set on a human body structure S, the tree structure acquisition unit 42 acquires a tree structure T of the human body structure S shown in FIG. 4. The tree structure T shown in FIG. 4 has a structure in which, with starting from a root node O, one branch b0 branches into three branches b1 to b3 at a branch point J1 and the branch b3 further branches into three branches b31 to b33 at a branch point J2.

Figure 5:
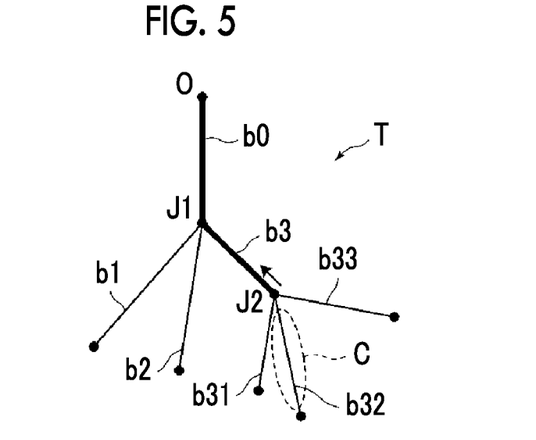
FIG. 5 is a diagram illustrating a branch upstream side of the target place on the tree structure.
Figure 6:
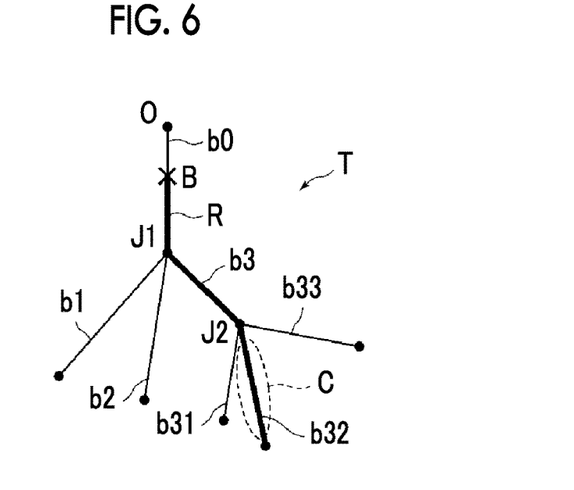
FIG. 6 is a diagram showing an example of a path from a reference point to a target place.

The path determination unit 43 determines a path from a reference point set on a branch upstream side of the target place to the target place in the acquired tree structure. The branch upstream side of the target place refers to a side toward the root of the tree structure from the target place through a branch of a branch source. For example, in the tree structure T shown in FIG. 4 in which a branch b32 is set as the target place C, since a section indicated by a bold line in FIG. 5 corresponds to the branch upstream side of the target place C, as shown in FIG. 6, the path determination unit 43 sets a reference point B in this section and determines a path R from the reference point B to the target place C. In FIG. 6, the path R is indicated by a bold line.

At this time, the reference point may be set at a position (root) of a start point of the tree structure, or may be set at a position as a reference for understanding the target place and at least an anatomical structure of the human body structure around the target place. For example, in a case where the target place is an artery, the reference point can be set at a position corresponding to an aorta on the tree structure, and in a case where the target place is a vein, the reference point can be set at a position corresponding to a vena cava on the tree structure. At this time, as the position corresponding to the aorta or the vena cava, a position on the tree structure arbitrarily determined as a position representing the aorta or the vena cava can be used. In a case where the target place is a portal vein, the reference point can be set at a position corresponding to the region of origin of the portal vein on the tree structure. In a case where the target place is a bronchus, the reference point can be set at a position corresponding to a trachea on the tree structure.

The priority setting unit 44 sets the priority for each branch of the acquired tree structure branching from the determined path. Specifically, the priority of each branch branching from the path can be set to be higher when the position of the branch is closer to the target place. This means that, in the case shown in FIG. 6, the priority of each of the branches b31 and b33 branching from the path R at the branch point J2 closest to the target place C is set to be higher than the priority of each of the branches b1 and b2 branching from the path R at the branch point J1 next closest to the target place C.

At this time, in a case where there are a plurality of branches at the same branch position branching from the path, the priority of each branch can be set by any method of (1) a method of setting the same priority for the branches at the same branch position, (2) a method of setting the priority such that, the shorter the distance between a middle point of a target branch and a middle point of a branch including the target place, the higher the priority, (3) a method of setting the priority such that, the larger the diameter (thickness) of the human body structure in the target branch, the higher the priority, and (4) a method of creating a table in which the priority of each branch is determined in advance for each group of branches branching at the same position on the tree structure, storing the table in the storage 4 or the like, and setting the priority according to the priority determined in the table.

For example, in the case shown in FIG. 6, according to the method of (1) described above, the priority is set in two steps of "branch b31, b33"→"branch b1, b2". In the case shown in FIG. 6, on an assumption that the distance between a middle point of the branch b31 and a middle point of the branch b32 including the target place is shorter than the distance between a middle point of the branch b33 and the middle point of the branch b32 including the target place, and the distance between a middle point of the branch b2 and the middle point of the branch b32 including the target place is shorter than the distance between a middle point of the branch b1 and the middle point of the branch b32 including the target place, according to the method of (2) described above, the priority is set in four steps of "branch b31"→"branch b33"→"branch b2"→"branch b1".

In the case shown in FIG. 6, on an assumption that, in the table in which the priority of each branch is determined in advance for a group of branches branching at the same position on the tree structure, the priority of each of the branches b1 to b3 branching at the branch point J1 are determined to be "branch b1"→"branch b2"→"branch b3", and the priority of each of the branches b31 to b33 branching at the branch point J2 is determined to be "branch b31"→"branch b32"→"branch b33", according to the method of (4) described above, the priority is set in four steps of "branch b31"→"branch b33"→"branch b2"→"branch b2".

The image generation unit 45 generates, from the three-dimensional image of the patient, an initial image representing only a portion of the determined path in the entire target human body structure and images for confirmation of each step in which the respective portions of the human body structure outside the path are displayed in an order of priority determined by the priority setting unit 44. At this time, in regards to the images for confirmation, although the images for confirmation of all steps may be generated in conformity with when generating the initial image, each image for confirmation may be generated each time at the timing at which the image for confirmation is required for display by the image generation unit 45 described below.

The image generation unit 45 can generate various images, such as a maximum intensity projection image (MIP image), a minimum intensity projection image (MinIP image), a surface-rendering image (SR image), and a volume-rendering image (VR image), as the initial image and the images for confirmation. The image generation unit 45 may generate, as as the initial image and the images for confirmation, still images in which a portion of the human body structure to be displayed in each image is drawn, or animations (motion pictures) in which a state of drawing a portion of the human body structure to be displayed step by step is expressed. For example, as the initial image, an animation in which a state of drawing a portion of the human body structure of the path from the reference point side step by step is expressed can be generated, and as the images for confirmation, animations in which a state of drawing portions of the human body structure outside the path from the branch point side step by step is expressed can be generated.

The display control unit 46 sequentially displays the initial image and the images for confirmation generated by the image generation unit 45 on the display device 5. Specifically, first, the initial image is displayed, and then, the images for confirmation are displayed such that the portions of the respective branches of the human body structure branching from the path are displayed in a descending order of priority determined by the priority setting unit 44.

Figure 7:
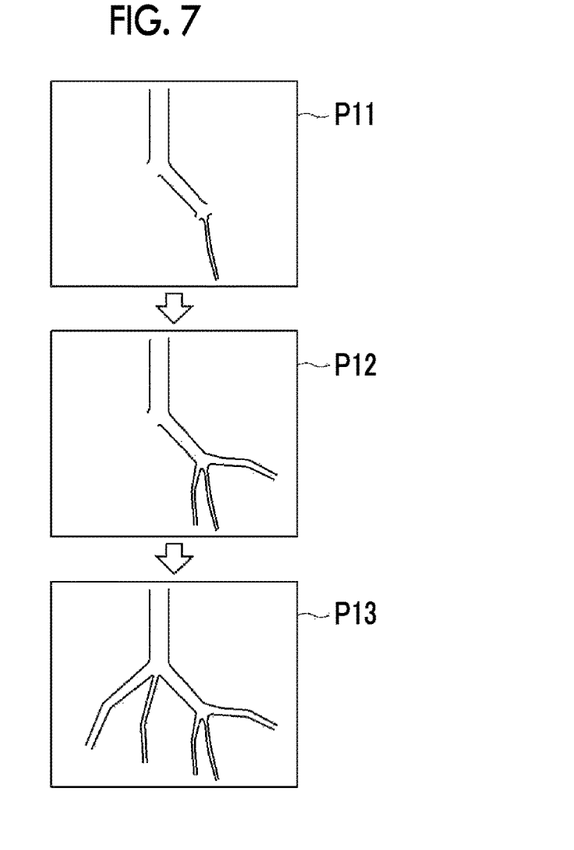
FIG. 7 is a diagram (first view) showing an example of display by a display control unit.
Figure 8:
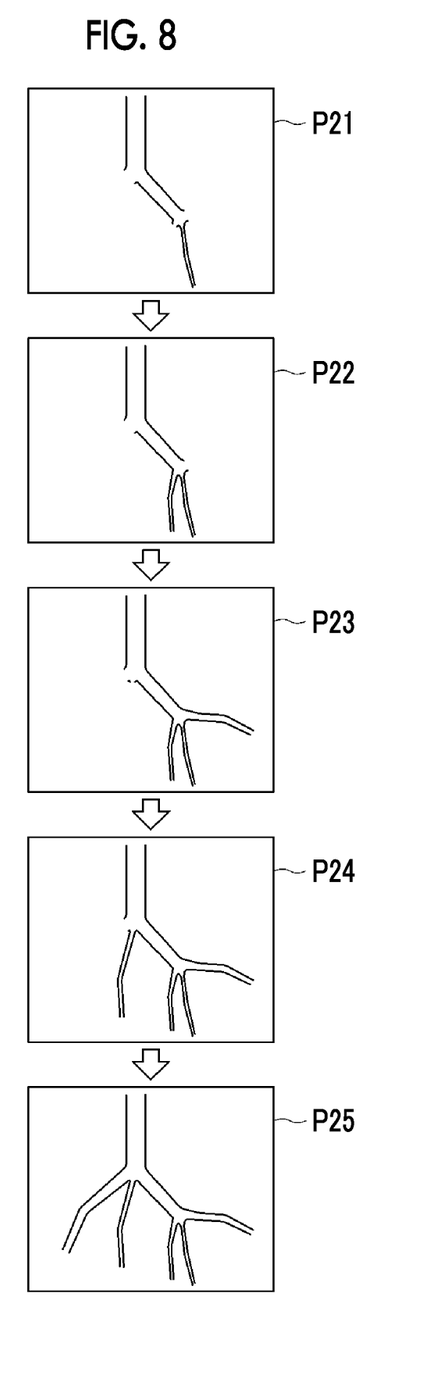
FIG. 8 is a diagram (second view) showing an example of display by the display control unit.
Figure 9:
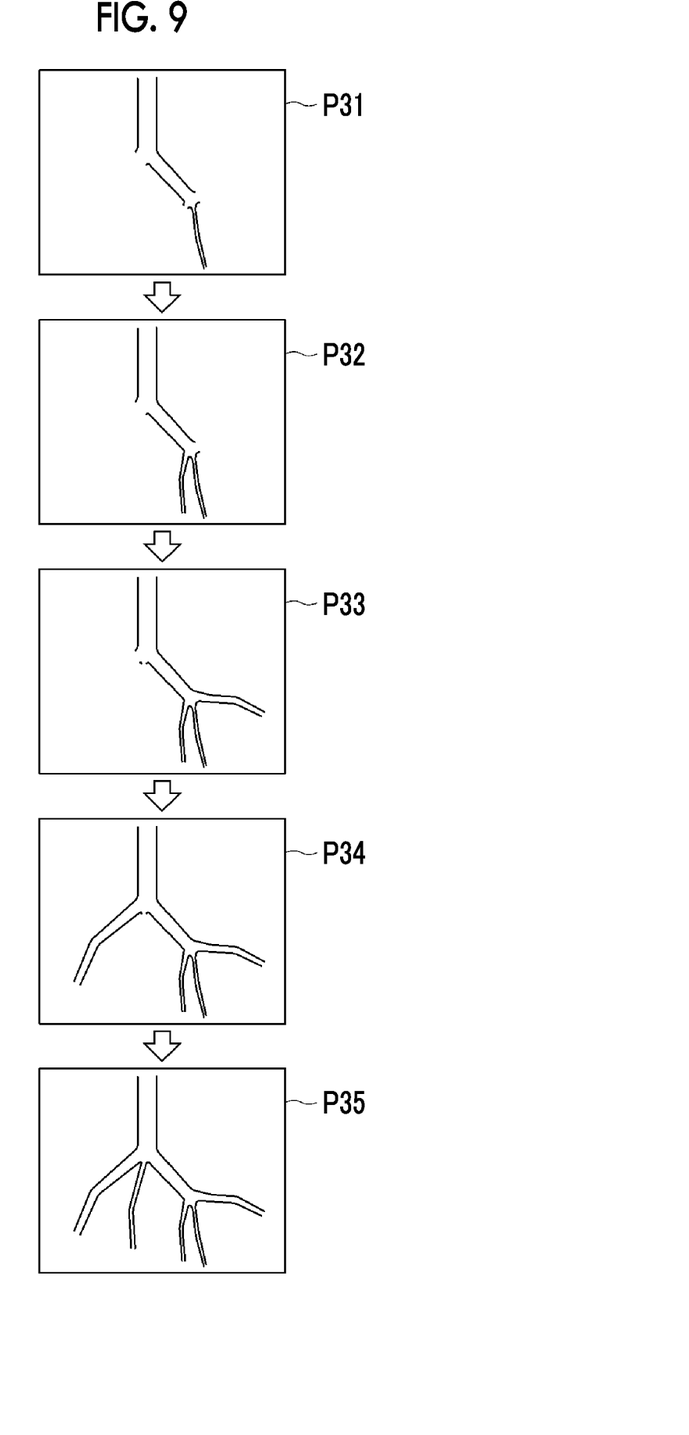
FIG. 9 is a diagram (third view) showing an example of display by the display control unit.

FIGS. 7 to 9 are respectively diagrams showing a specific example of display by the display control unit 46. FIG. 7 is a diagram showing an example where, in the case shown in FIG. 6, an initial image P11 representing only a portion of the path R in the entire human body structure S and images P12 and P13 for confirmation of each step, in which the respective portions of the human body structure S outside the path R are gradually displayed in an order of "branch b31, b33"→"branch b1, b2" as the priority determined by the method of (1) described above, generated by the image generation unit 45 are displayed.

FIG. 8 shows an example where, in the case shown in FIG. 6, an initial image P21 representing only a portion of the path R in the entire human body structure S and images P22 to P25 for confirmation of each step, in which the respective portions of the human body structure S outside the path R are gradually displayed in an order of "branch b31"→"branch b33"→"branch b2"→"branch b1" as the priority determined by the method of (2) described above, generated by the image generation unit 45 are displayed. FIG. 9 shows an example where, in the case shown in FIG. 6, an initial image P31 representing only a portion of the path R in the entire human body structure S and images P32 to P35 for confirmation of each step, in which the respective portions of the human body structure S outside the path R are gradually displayed in an order of "branch b31"→"branch b33"→"branch b1"→"branch b2" as the priority determined by the method of (4) described above, generated by the image generation unit 45 are displayed.

The display control unit 46 can perform processing for switching and displaying the images for confirmation next to the initial image automatically or manually. In a case of automatic switching, conditions for automatic switching and display, for example, a switching start timing, a rate, and the like, can be set, and display switching processing can be executed by the computer according to the setting. The display control unit 46 may further perform processing (reverse-order display) for, after processing (forward-order display) for displaying the images for confirmation next to the initial image in a descending order of priority ends, displaying these images in a reverse order again. The display control unit 46 may repeatedly perform the forward-order display and the reverse-order display.

In a case of manual switching, the display control unit 46 can first display the initial image, and next, each time there is an input from an operator instructing display switching, can display the images for confirmation in a display order such that the portions of the respective branches of the human body structure branching from the path are displayed in a descending order of priority. In addition, the display control unit 46 may display the images for confirmation in the display order (forward order) according to an input from the operator instructing to display the images for confirmation in the display order (forward order) and may display the images for confirmation image for confirmation in a reverse display order (reverse order) to the display order according to an input from the operator instructing to display the images for confirmation in the reverse display order (reverse order) to the display order. For example, the display can be switched to the next image for confirmation in the display order (forward order) according to a user's operation to rotate a wheel of the mouse in a backward direction, and the display can be switched to the immediately preceding image for confirmation in the display order (forward order) according to a user's operation to rotate the wheel of the mouse in a forward direction. Of course, the display control unit 46 can perform the same display switching processing according to an input from another input device, such as a keyboard.

Figure 10:
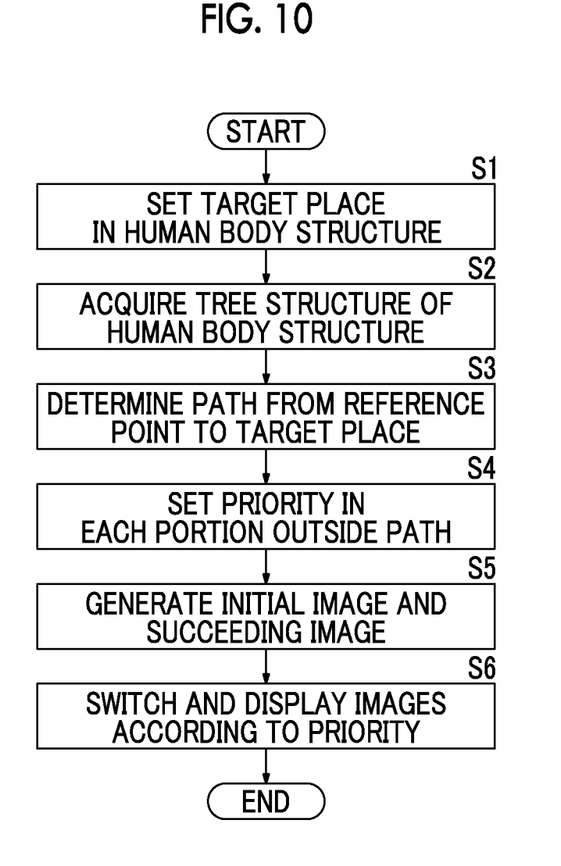
FIG. 10 is a flowchart showing the flow of processing in the image processing device of FIG. 1.

Next, the flow of the processing in the image processing device 1 will be described referring to the flowchart shown in FIG. 10. First, the target place setting unit 41 sets the target place in the area of the human body structure in the three-dimensional image of the patient obtained by imaging the human body structure having the tree structure, such as a bronchus, a blood vessel, or a bone (S1). Next, the tree structure acquisition unit 42 acquires the tree structure of the human body structure including the target place set in Step S1 from the three-dimensional image of the patient (S2). Next, the path determination unit 43 sets the reference point on the branch upstream side of the target place in the tree structure acquired in Step S2 and determines the path from the set reference point to the target place (S3). Next, the priority setting unit 44 sets the priority for each branch of the tree structure branching from the path determined in Step S3 described above (S4). The priority setting unit 44 sets the priority of each branch branching from the path such that, the closer the position of the branch to the target place, the higher the priority. In a case where there are a plurality of branches at the same branch position branching from the path, the priority of each branch is set by any method of (1) to (4) described above. Next, the image generation unit 45 generates, from the three-dimensional image of the patient, the initial image representing only the portion of the path in the entire human body structure and the images for confirmation of each step in which the respective portions of the human body structure outside the path are displayed in an order of priority determined in Step S4 (S5). Finally, the display control unit 46 sequentially displays the initial image and the images for confirmation generated in Step S5 on the display device 5. The display control unit 46 first displays the initial image, and next, displays the images for confirmation such that the portions of the respective branches of the human body structure branching from the path are displayed in a descending order of priority determined in Step S4.

With the above configuration, according to the image processing device 1 of this embodiment, the target place setting unit 41 sets the target place in the area of the human body structure in the three-dimensional image obtained by imaging the human body structure having the tree structure, the tree structure acquisition unit 42 acquires the tree structure of the human body structure in the three-dimensional image, the path determination unit 43 determines the path from the reference point set on the branch upstream side of the target place on the acquired tree structure to the target place, the image generation unit 45 generates, from the three-dimensional image, the initial image representing only the portion of the determined path in the entire human body structure and the images for confirmation of each step sequentially representing the respective portions of the human body structure outside the determined path according to the priority determined based on the positional relationship with the target place, and the display control unit 46 displays the generated initial image on the display unit and then displays the generated images for confirmation on the display unit such that the respective portions of the human body structure outside the path are sequentially displayed according to the priority determined based on the positional relationship with the target place. With this display, it is possible to allow the user to easily understand what anatomical region a place of interest on a human body structure is or what kind of anatomical structure there is around the place.

Figure 11:
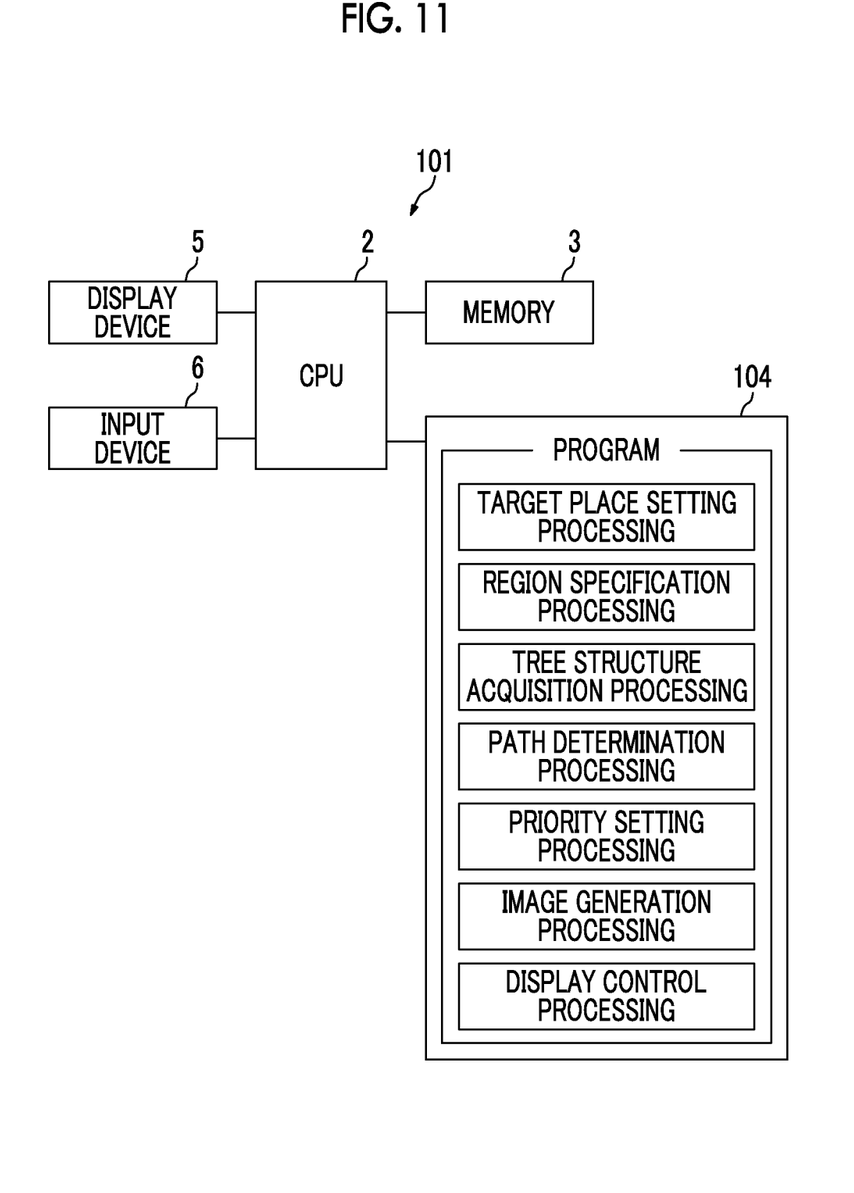
FIG. 11 is a diagram showing the schematic configuration of an image processing device according to a second embodiment.
Figure 12:
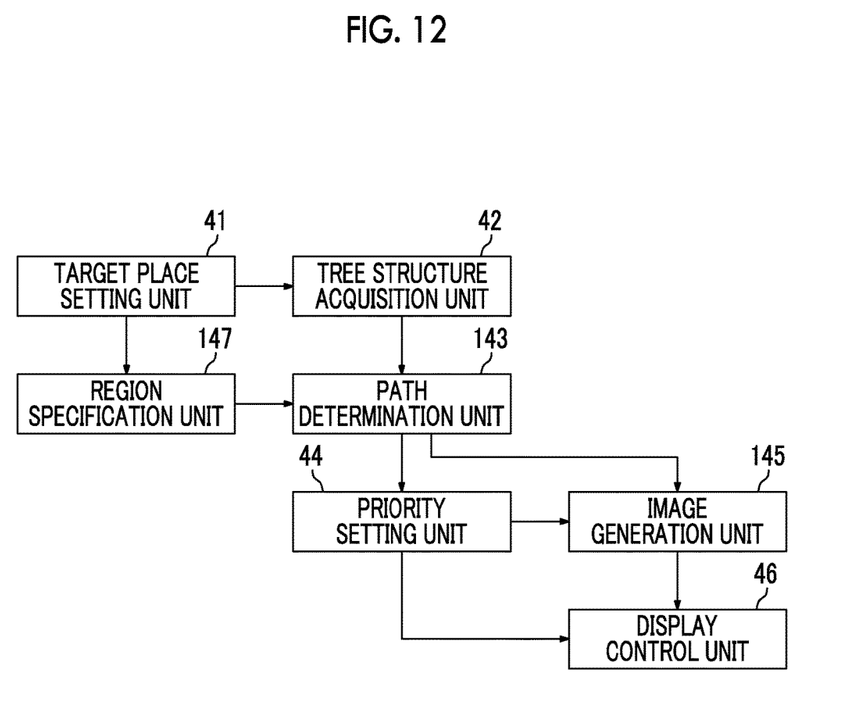
FIG. 12 is a block diagram showing functions mounted in the image processing device of FIG. 11.

Next, a second embodiment of an image processing device of the invention will be described referring to FIGS. 11 and 12. FIG. 11 is a schematic configuration diagram showing an image processing device 101 according to the second embodiment, and FIG. 12 schematically shows functions mounted in the image processing device 101 into blocks. The same components as those in the first embodiment are represented by the same reference numerals, and description thereof will not be repeated.

The second embodiment is different from the first embodiment in that a region of a human body to which a target place belongs is specified, the path is determined in consideration of the display range corresponding to the specified region of the human body, and an initial image and images for confirmation representing the display range are generated. Hereinafter, the details of this difference will be described.

In this embodiment, as shown in FIG. 11, an image processing program stored in a storage 104 further defines, as processing to be executed on the CPU, region specification processing for specifying a region of a human body to which a target place belongs, in addition to the target place setting processing, the tree structure acquisition processing, the path determination processing, the priority setting processing, the image generation processing, and the display control processing. According to the definition of the program, the CPU executes the respective kinds of processing, whereby the computer functions as a target place setting unit 41, a tree structure acquisition unit 42, a path determination unit 143, a priority setting unit 44, an image generation unit 145, a display control unit 46, and a region specification unit 147 as shown in FIG. 12. In this embodiment, a table in which each region of the human body and a display range are made to correspond to each other is created in advance and stored in the storage 104. In this table, for example, a display range called "liver area" can be defined to correspond to "liver", and a display range called "lung area" can be defined to correspond to "bronchus".

If the target place is set by the target place setting unit 41, the region specification unit 147 specifies a region of the human body to which the target place belongs to. The region specification unit 147 can specify the region, to which the target place belong, automatically or manually. In a case of automatic specification, the computer can execute processing for automatically recognizing the region, to which the target place belongs, by image analysis to specify the recognized region as the region to which the target place belongs. For example, it is possible to recognize the region, to which the target place belongs, from the three-dimensional image of the patient using a region recognition method described in A. Criminisi et al., "Regression Forests for Efficient Anatomy Detection and Localization in CT Studies", Medical Computer Vision. Recognition Techniques and Applications in Medical Imaging, Lecture Notes in Computer Science, Vol. 6533, pp. 106-117, 2011.

In a case of manual specification, for example, options of the region can be displayed on the display device 5, an input from the user to select (designate) any region can be received, and the designated part can be specified as the region to which the target place belongs.

The path determination unit 143 sets the reference point at the uppermost position in the tree structure within the display range corresponding to the region of the human body specified by the region specification unit 147 and determines the path from the reference point to the target place. Information of the display range corresponding to the region of the human body can be acquired referring to the display range corresponding to the region of the human body specified by the region specification unit 147 from the table stored in the storage 104 in which each region of the human body and the display range are made to correspond to each other.

The image generation unit 145 generates, from the three-dimensional image of the patient, the initial image representing only the portion of the determined path in the entire target and the images for confirmation of each step in which the respective portions of the human body structure outside the path are displayed in an order of priority determined by the priority setting unit 44 with the display range corresponding to the region of the human body specified by the region specification unit 147 as a drawing range.

With the above configuration, according to the image processing device 101 of this embodiment, the target place setting unit 41 sets the target place in the area of the human body structure in the three-dimensional image obtained by imaging the human body structure having the tree structure, the region specification unit 147 specifies the region of the human body to which the target place belongs, the tree structure acquisition unit 42 acquires the tree structure of the human body structure in the three-dimensional image, the path determination unit 143 sets the reference point at the uppermost position in the tree structure within the display range corresponding to the region of the human body specified by the region specification unit 147 and determines the path from the reference point to the target place, the image generation unit 145 generates, from the three-dimensional image, the initial image representing only the portion of the determined path in the entire human body structure and the images for confirmation of each step sequentially representing the respective portions of the human body structure outside the path according to the priority determined based on the positional relationship with the target place with the display range as the drawing range, and the display control unit 46 displays the generated initial image on the display unit and then displays the generated images for confirmation on the display unit such that the respective portions of the human body structure outside the path are sequentially displayed according to the priority determined based on the positional relationship with the target place. With this display, it is possible to allow the user to easily understand what anatomical region a place of interest on a human body structure is or what kind of anatomical structure there is around the place. Furthermore, in this embodiment, as described above, the region of the human body to which the target place belongs is specified, and the initial image and the images for confirmation are generated and displayed with the display range corresponding to this region as the drawing range. With this display, it is possible to allow the user to more easily observe a region to be observed.

In the respective embodiments described above, although a case where the images for confirmation of each step in which the respective portions of the human body structure outside the path determined by the path determination unit 43 are gradually displayed in an order of priority are generated from the three-dimensional image of the patient and displayed has been described, alternatively, for example, the images for confirmation of each step in which the respective portions of the human body structure outside the path are displayed to be sequentially switched in an order of priority may be generated and displayed. Furthermore, the user may appropriately switch between both display modes by settings or the like.

In the respective embodiments described above, although a case where an initial image, in which only the portion of the determined path in the entire human body structure is a display target and other portions are non-displayed, and images for confirmation, in which the respective portions of the human body structure outside the path are a display target gradually or to be switched in an order of priority in addition to the portion of the path and other portions are continuously non-displayed, are generated and displayed has been described, alternatively, for example, an initial image in which only a portion of the path is displayed in an enhanced mode whereas the entire human body structure is constantly a target to be displayed and images for confirmation of each step in which the respective portions of the human body structure outside the path are displayed gradually or to be switched in an enhanced mode in an order of priority in addition to the portion of the path may be generated and displayed. At this time, a portion other than the portion displayed in the enhanced mode may be displayed in a more obtrusive mode. For example, a portion to be enhanced may be displayed to be nontransparent and other portions may be displayed to be semitransparent, and in addition or alternatively, the enhanced portion may be displayed in a color with high brightness and/or saturation and other portions may be displayed in a color with low brightness and/or saturation.

In the respective embodiments described above, although a case where the reference point is set on the branch upstream side of the target place on the tree structure and the path from the reference point to the target place is determined has been described, the reference point may be set at a place other than the branch upstream side and the path may be determined. For example, in the case shown in FIG. 5, the reference point may be set in a portion other than the section corresponding to the branch upstream side of the target place C indicated by the bold line, for example, within the section of the branch b1 or the branch b2, and the path from the set reference point to the target place may be determined.

In the respective embodiments described above, although a case where an image for observing a place of interest in the human body structure having the tree structure is provided has been described, the image processing device, method, and program of the invention can also be applied to a case of observing a place of interest in a human body structure having a graph structure including a loop structure.

What is claimed is:
1. An image processing device comprising:
a processing circuitry configured to:
set a target place in an area of a human body structure having a tree structure in a three-dimensional image obtained by imaging the human body structure;
extract the tree structure of the human body structure from the three-dimensional image;

determine a path from a reference point set on a branch upstream side of the target place on the extracted tree structure to the target place;

set priority for respective branches that branch off at branch points of the tree structure of the human body structure outside the path based on a positional relationship between the branches and the target place;

generate, from the three-dimensional image, an initial image representing only a portion of the determined path in the entire human body structure and images for confirmation of the respective branches of the human body structure outside the path;

a display device which displays an image; and a display controller which displays the generated initial image on the display device and then displays the generated images for confirmation of each step on the display device such that the respective portions of the human body structure outside the path are sequentially displayed according to the priority, wherein the processing circuitry sets the priority such that, that branches at positions closer to the target place have higher priority than branches at positions further from the target place, wherein the processing circuitry generates, from the three-dimensional image, the images for confirmation of each step in which the respective branches of the human body structure branching from the path are displayed in an order of the priority determined by the processing circuitry, and wherein the display controller displays the generated images for confirmation on the display device such that the respective branches of the human body structure branching from the path are displayed in a descending order of the determined priority.

2. The image processing device according to claim 1, wherein, in a case where there are a plurality of branches at a same branch position branching from the path, the processing circuitry sets the priority for each of the plurality of branches such that, the shorter the distance between a middle point of the branch and a middle point of a branch including the target place, the higher the priority.

3. The image processing device according to claim 1, wherein the processing circuitry accesses a table in which the priority of each branch is determined in advance for each group of branches branching at a same position on the tree structure, and in a case where there are a plurality of branches at the same branch position branching from the determined path, sets the priority determined in the table.

4. The image processing device according to claim 1, wherein the display controller displays the images for confirmation in a display order according to an input from an operator instructing to display the images for confirmation in the display order such that the respective branches are displayed in a descending order of the priority and displays the images for confirmation in a reverse display order to the display order according to an input from the operator instructing to display the images for confirmation in the reverse display order to the display order.

5. The image processing device according to claim 1, the processing circuitry further configured to specify a region of a human body, to which the target place belongs; and the image processing device further comprises a storage which stores a table, in which each region of the human body and a display range are made to correspond to each other, wherein the processing circuitry generates the initial image and the images for confirmation of each step representing the display range corresponding to the specified region of the human body from the three-dimensional image based on the table.

6. The image processing device according to claim 5, wherein the processing circuitry determines the path by setting the reference point at an uppermost position in the tree structure within the display range corresponding to the specified region of the human body.

7. The image processing device according to claim 1, wherein, in a case where an aorta is included in the human body structure and the target place is an artery, the processing circuitry determines the path by setting the reference point at a position corresponding to the aorta on the tree structure.

8. The image processing device according to claim 1, wherein, in a case where the region of origin of a portal vein is included in the human body structure and the target place is the portal vein, processing circuitry determines the path by setting the reference point at a position corresponding to the region of origin of the portal vein on the tree structure.

9. The image processing device according to claim 1, wherein the processing circuitry determines the path by setting the reference point at a position of a starting point of the acquired tree structure.

10. An image processing method comprising:

a step of setting a target place in an area of a human body structure having a tree structure in a three-dimensional image obtained by imaging the human body structure;

a step of extracting the tree structure of the human body structure from the three-dimensional image;

a step of determining a path from a reference point set on a branch upstream side of the target place on the extracted tree structure to the target place;

a step of setting priority for respective branches that branch off at branch points of the tree structure of the human body structure outside the path based on a positional relationship between the branches and the target place;

a step of generating, from the three-dimensional image, an initial image representing only a portion of the determined path in the entire human body structure and images for confirmation of the respective branches of the human body structure outside the path; and a step of displaying the generated initial image on a display device and then displaying the generated images for confirmation of each step on the display device such that the respective portions of the human body structure outside the path are sequentially displayed according to the priority, wherein the step of setting priority sets the priority such that branches at positions closer to the target place have higher priority than branches at positions further from the target place, wherein the step of generating the initial image generates, from the three-dimensional image, the images for confirmation of each step in which the respective branches of the human body structure branching from the path are displayed in an order of the determined priority, and wherein the step of displaying displays the generated images for confirmation on the display device such that the respective branches of the human body structure branching from the path are displayed in a descending order of the determined priority.

11. A non-transitory computer readable recording medium having stored therein an image processing program which causes a computer to perform a method comprising:
  setting a target place in an area of a human body structure having a tree structure in a three-dimensional image obtained by imaging the human body structure;
  extracting the tree structure of the human body structure from the three-dimensional image;
  determining a path from a reference point set on a branch upstream side of the target place on the extracted tree structure to the target place;
  set priority for respective branches that branch off at branch points of the tree structure of the human body structure outside the path based on a positional relationship between the branches and the target place;
  generating, from the three-dimensional image, an initial image representing only a portion of the determined path in the entire human body structure and images for confirmation of the respective branches of the human body structure outside the determined path; and
  displaying the generated initial image on a display device and then display the generated images for confirmation of each step on the display device such that the respective portions of the human body structure outside the path are sequentially displayed according to the priority,
  wherein the priority is set such that branches at positions closer to the target place have higher priority than branches at positions further from the target place,
  wherein, from the three-dimensional image, the images for confirmation of each step are generated in which the respective branches of the human body structure branching from the path are displayed in an order of the determined priority, and
  wherein the generated images are displayed for confirmation on the display device such that the respective branches of the human body structure branching from the path are displayed in a descending order of the determined priority.

* * * * *